United States Patent [19]
Rivera

[11] Patent Number: 5,516,696
[45] Date of Patent: May 14, 1996

[54] METHOD AND COMPOSITION FOR INDICATING THE PRESENCE OF CHROME-FREE PRETREATMENTS ON METAL SURFACES BY FLUORESCENCE

[75] Inventor: Jos" B. Rivera, Philadelphia, Pa.

[73] Assignee: Bulk Chemicals, Inc., Leesport, Pa.

[21] Appl. No.: 305,195

[22] Filed: Sep. 13, 1994

[51] Int. Cl.⁶ .................................................. G01N 21/76
[52] U.S. Cl. ................................ 436/56; 436/2; 436/172
[58] Field of Search ................................. 436/2, 56, 172; 250/302; 148/241, 247

[56] References Cited

U.S. PATENT DOCUMENTS

| | | | |
|---|---|---|---|
| 3,956,630 | 5/1976 | Mellows | 250/302 |
| 4,191,596 | 3/1980 | Dollman et al. | 148/247 |
| 4,250,382 | 2/1981 | Libby | 250/302 |
| 4,313,769 | 2/1982 | Frelin et al. | 148/6.27 |
| 4,327,120 | 4/1982 | Siemers et al. | 427/34 |
| 4,327,155 | 4/1982 | Hanneman | 428/556 |
| 4,338,140 | 7/1982 | Reghi | 148/6.14 R |
| 4,711,667 | 12/1987 | Bibber | 106/14.21 |
| 4,878,963 | 11/1989 | Bibber | 148/262 |
| 4,885,254 | 12/1989 | Sung | 436/85 |
| 4,895,608 | 1/1990 | Bibber | 428/427.2 |
| 5,000,802 | 3/1992 | Mickols | 436/34 |
| 5,089,064 | 2/1992 | Reghi | 148/247 |
| 5,129,967 | 7/1992 | Sander et al. | 148/247 |
| 5,194,138 | 3/1993 | Mansfeld et al. | 205/183 |
| 5,225,675 | 7/1993 | O'Donnell | 250/302 |
| 5,292,378 | 3/1994 | Ouyang et al. | 148/241 |
| 5,342,456 | 8/1994 | Dolan | 148/247 |

OTHER PUBLICATIONS

D. A. Jones, "Principles and Prevention of Corrosion", Macmillan Publishing Co., 1992 (pp. 43, 85–92).

*Primary Examiner*—Jill Warden
*Assistant Examiner*—Sharidan Carrillo
*Attorney, Agent, or Firm*—Ratner & Prestia

[57] ABSTRACT

A method and composition for indicating the presence of a chrome-free pretreatment for improving the paint adhesion and corrosion resistance of a metal surface. The presence of the pretreatment is indicated by adding a compound to the chrome-free pretreatment which causes the pretreatment to fluoresce under an ultraviolet light. The additive which causes the pretreatment to fluoresce under an ultraviolet light is an ultraviolet tracer, such as a stilbene or a coumarin derivative, and the method according to this invention includes exposing the coated metal to ultraviolet light.

4 Claims, 1 Drawing Sheet

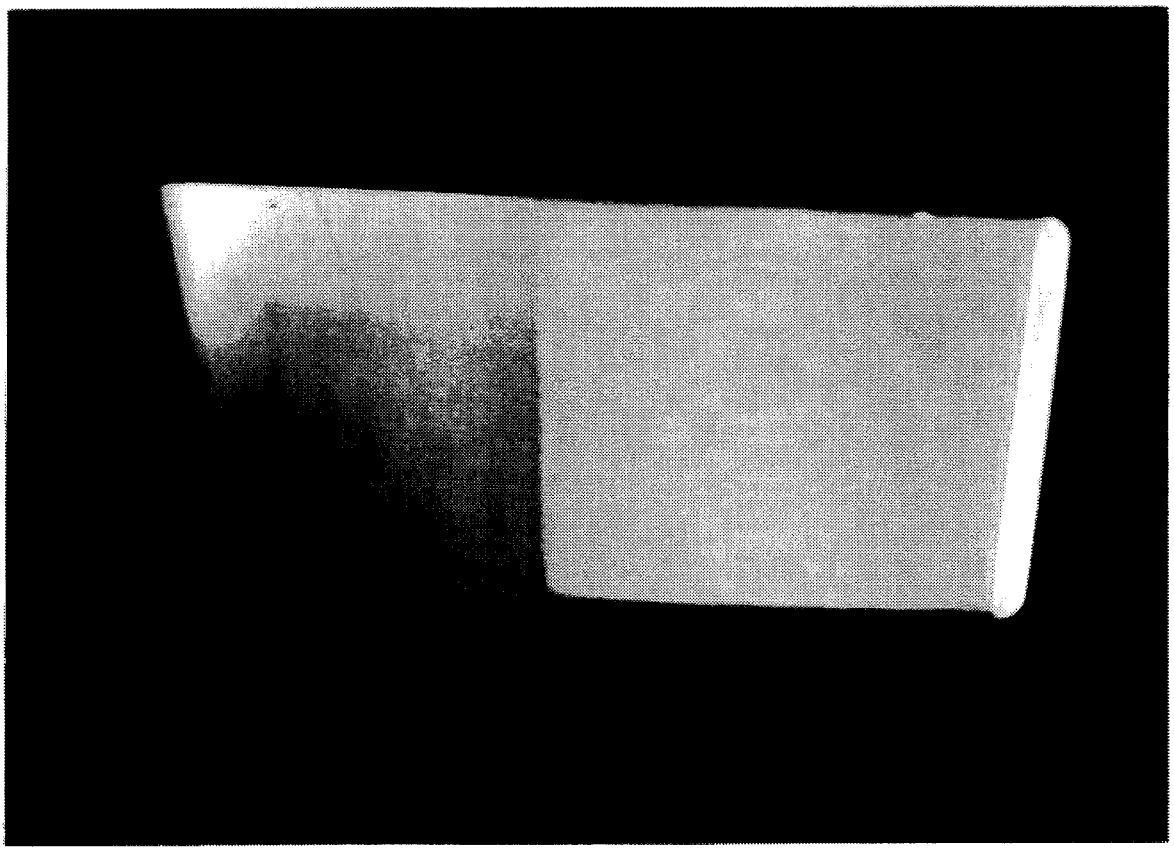

METHOD AND COMPOSITION FOR INDICATING THE PRESENCE OF CHROME-FREE PRETREATMENTS ON METAL SURFACES BY FLUORESCENCE

FIELD OF THE INVENTION

The present invention pertains to a method and composition for indicating the presence of a chrome-free pretreatment on a metal surface. More particularly, the present invention involves adding a compound to the chrome-free pretreatment which causes the pretreatment to fluoresce under an ultraviolet light.

BACKGROUND OF THE INVENTION

Before chromium was recognized as environmentally hazardous, compositions containing chromium were used as coatings for improving the corrosion resistance and paint adhesion of metals. Chromium chromate and chromium phosphate were two compounds typically used as coatings for metal. One advantageous side effect of these compounds was that they left a slight coloration on the coated metal, thereby assuring the user that the coating was in fact applied to the metal.

Recent developments led to the use of chrome-free coatings, or "pretreatments," which are typically based on the fluo or oxy-fluo forms of group IV-B elements of the periodic table (e.g., titanium, zirconium, and hafnium). These chrome-free pretreatments provide surface coatings whose compositions are based on the products of the interaction between the metallic substrate and these group IV-B compounds.

While chrome-free pretreatments have been commercially successful, one of the major objections to this technology has been that chrome-free pretreatments leave little or no color on the metal, unlike the previously used chromium compositions. Thus, the only indication to the user that the pretreatment has been applied to the metal is surface appearance characteristics, such as uniformity of wetting and a viscous fluid surface film. Even at extreme deposition (i.e. high coating weight) of chrome-free pretreatments, where a slight indication of coloration is present, the coloration is so faint that it is of no practical use. Accordingly, because chrome-free pretreatments show little or no coloration, the user has no option other than analytical methods to determine the presence and the amount of pretreatment on the metal surface.

SUMMARY OF THE INVENTION

The present invention provides a means by which chrome-free pretreatments on metallic substrates can be made detectable to the naked eye by providing coloration to an otherwise colorless pretreated metallic surface. The present invention also provides a diagnostic tool for determining the effectiveness and uniformity of the application of the pretreatment to the metallic substrate.

To achieve these and other objects, and in view of its purposes, the present invention provides a method and composition for indicating the presence of a chrome-free pretreatment on a metal surface. The composition of the present invention includes a chrome-free pretreatment comprising a polymeric resin and a group IV-B compound and an ultraviolet tracer, such as a stilbene or a coumarin derivative, which exhibits a color upon exposure to ultraviolet light. The method of the present invention includes forming a mixture of a chrome-free pretreatment comprising a polymeric resin and a group IV-B compound and an ultraviolet tracer, such as a stilbene or a coumarin derivative, which exhibits a color upon exposure to ultraviolet light, and then applying the mixture to a metal surface to form a coated metal surface. Thereafter, the coated metal surface is exposed to ultraviolet light.

It is to be understood that both the foregoing general description and the following detailed description are exemplary, but are not restrictive, of the invention.

BRIEF DESCRIPTION OF THE DRAWING

The file of this patent contains at least one drawing executed in color. Copies of this patent with color drawings will be provided by the Patent and Trademark Office upon request and payment of the necessary fee.

The invention is best understood from the following detailed description when read in connection with the accompanying drawing, in which the FIGURE is a photograph of a sample of aluminum which was treated by a composition of the present invention and exposed to ultraviolet light.

DETAILED DESCRIPTION OF THE INVENTION

This invention provides a method and composition for indicating the presence of the otherwise not visible chrome-free pretreatment on a metallic surface. This invention also provides a method and composition for estimating the amount of the chrome-free pretreatment applied and the uniformity of its application.

As used herein, the term "chrome-free pretreatment" means any solution which improves the paint adhesion and corrosion resistance of a metal surface and which does not include chromium in any form. The chrome-free pretreatment used in connection with the present invention comprises a polymeric resin and a group IV-B compound. The term "polymeric resin" means any polymer which is conventionally used in connection with pretreatments for improving the paint adhesion and corrosion resistance of a metal surface and which is soluble in water or capable of being dispersed in water. The term "group IV-B compound" means either an acid or a salt of a Group IV-B element. Such acids include hydrofluozirconic acid ($H_2ZrF_6$), fluotitanic acid ($H_2TiF_6$) and fluohafnic acid ($H_2HfF_6$). An exemplary salt of a Group IV-B element is ammonium zirconium carbonate. An ammonium zirconium carbonate solution sold by Magnesium Elektron Inc. under the trademark BACOTE 20, having a working empirical formula of $(NH_4)_2[Zr(OH)_2(CO_3)_2]+nH_2O$, may be used in connection with the present invention.

An exemplary chrome-free pretreatment which may be used in connection with the present invention is the composition of the assignee's co-pending patent application Ser. No. 08/112,890, filed on Aug. 27, 1993, and entitled A METHOD AND COMPOSITION FOR TREATING METAL SURFACES, which is incorporated herein by reference. The "polymeric resin" is the ester cross-linked polymer system of the '890 patent application which includes a plurality of carboxylic functional groups and a plurality of hydroxyl functional groups. Another exemplary polymeric resin is the composition disclosed in Table 2 of the '890 patent application, which is an aqueous solution of polyacrylic acid, ammonium bifluoride, and a fluosurfactant. Another exemplary chrome-free pretreatment is the pretreatment disclosed in U.S. Pat. No. 4,191,596 to Dollman et al., which includes a fluo acid and a carboxylic polymer. Still another exemplary chrome-free pretreatment is the pretreatment disclosed in U.S. Pat. No. 5,129,967 to Sander et al., which includes dihydrohexafluozirconic acid, dihydrohexafluotitanic acid, polyacrylic acid, and hydrofluoric acid. Yet another exemplary chrome-free pretreatment which may be used in connection with the present invention is the pretreatment sold under the trademark OAKEMCOAT™ by Oakire Products, Inc.

The composition of present invention may be used on a wide variety of metals, including, but not limited to, aluminum and aluminum alloys, zinc and zinc alloys, iron and iron alloys, and combinations thereof. Also, the composition of the present invention may be applied to the metal surface by any known coating technique, including spray, immersion, roll coating, or flow coating techniques.

The additive used in the present invention should be capable of exhibiting a color, meaning that the pretreatment is no longer merely a clear solution, but fluoresces on exposure to an energy source, such as ultraviolet light. Even in the absence of color, however, the present invention can be used as a tag or marker to indicate the presence of a particular pretreatment coated on a metal. For example, if a stilbene derivative is used as the additive in a particular pretreatment, then a chemical analysis of the coating on a metal surface should reveal some level of the stilbene derivative in the coating, which would confirm that the particular pretreatment was actually used to coat that metal surface. In order to serve as a tag or marker, the additive must be otherwise absent in the system, which includes the chrome-free composition and the metal of the metal surface.

According to the present invention, the additive is an ultraviolet tracer which exhibits a color upon exposure to ultraviolet light, such as fluorescent whitening agents. One fluorescent whitening agent which has been used is a stilbene ($C_6H_5CH:CHC_6H_5$) derivative sold under the trademark LEUCOPHOR BCF Powder 115, by Sandoz Chemicals Corporation. Another fluorescent whitening agent which has been used is a stilbene derivative sold under the trademark EASTOBRITE® OB-1, sold by Eastman Chemical Products, Inc., and registered under C.A.S. Registration Number 1533-45-5. Other possible compounds which may be used are found in *McCutcheon's Volume 2: Functional Materials,* McCutcheon Division, MC Publishing Co., 1993, at pages 178 to 182 under the heading "Fluorescent Whitening Agents." These materials vary in solubility and dispersibility. The utility of any of these compounds will depend on their ability to be incorporated into a working bath of the chrome-free pretreatment. More particularly, the selected compounds should be soluble in the bath or capable of being dispersed in the bath.

According to the method of this embodiment of the invention, the ultraviolet tracer is added to the pretreatment which is subsequently applied to a metal surface, then the coated metal surface is exposed to ultraviolet light. The coated metal fluoresces upon exposure to ultraviolet light both while the pretreatment is still wet.

The additive may be always present in the working pretreatment bath to continuously indicate that the metal has been coated with the pretreatment. Alternatively, an operator could periodically add the additive to the working pretreatment bath and shortly thereafter observe the metal surface to detect the presence of and uniformity of the pretreatment on the metal surface.

According to the present invention, an ultraviolet light could be placed near the process at a point after the metal has been coated with the pretreatment.

Another advantage of the present invention is that the additive is immiscible with paint. As used herein, the term "immiscible" means that the additive does not mix with paint in a manner which would degrade the color, luster, or other characteristics of the paint. If an additive were used which does deleteriously mix with paint, then the color of the paint might be altered, which is undesirable.

EXAMPLES

The following examples are included to more clearly demonstrate the overall nature of the invention. These examples are exemplary, not restrictive, of the invention.

EXAMPLE 1

In order to show that an ultraviolet tracer can be used to indicate the presence of a chrome-free pretreatment on a metal surface, a stilbene derivative sold under the trademark LEUCOPHOR BCF Powder 115, by Sandoz Chemicals Corporation was blended with two parts deionized water and two parts isopropyl alcohol, thereby producing a 20% by weight solution. (The reason for this blending was to render this water insoluble stilbene derivative to become water dispersible.)

This solution was added to a chrome-free pretreatment according to the '890 patent application. In particular, this chrome-free pretreatment was an ester cross-link polymer system having both carboxylic and hydroxyl functional groups, along with fluozirconic acid. More particularly, the solution was 1.14 grams of solids for 1 liter of bath of a 1%/1% (by volume) solution. The solution was added to achieve a stilbene derivative concentration at the levels shown in Table 1 below and had the following UV characteristics when examined under ultraviolet light.

TABLE 1

| Amount of Stilbene derivative | UV Characteristic |
|---|---|
| 0.000 gm | None |
| 0.010 gm | Some fluorescence - gets better as drying takes place |
| 0.020 gm | Better than above - fluoresced to a blue color |
| 0.030 gm | Excellent - clearly fluoresced to a blue color |
| 0.050 gm | Excellent - clearly fluoresced to a blue color |

The sample with 0.050 gm of the stilbene derivative is shown in the FIGURE. The portion which was treated is the right side of the sample. This FIGURE shows that the inclusion of the stilbene derivative sold under the trademark LEUCOPHOR BCF Powder 115 in a chrome-free pretreatment fluorescences under an ultraviolet light, thereby indicating the presence of the pretreatment on the metal. According to this example, the stilbene derivative should be present in an amount of at least 0.010 grams/liter of working bath.

EXAMPLE 2

In order to show that an ultraviolet tracer can be used to indicate the presence of a chrome-free pretreatment on a metal surface, a stilbene derivative sold under the trademark EASTOBRITE® OB-1 by the Eastman Chemical Company was added to a chrome-free pretreatment according to the '890 patent application. In particular, this chrome-free pretreatment was an ester cross-link polymer system having both carboxylic and hydroxyl functional groups, along with fluozirconic acid. More particularly, the solution was 1.14 9rams of solids for 1 liter of bath of a 1%/1% (by volume) solution. The stilbene derivative was added at the levels shown in Table 2 below, dispersed in the bath, and had the following UV characteristics when examined under ultraviolet light.

TABLE 2

| Amount of Stilbene derivative | UV Characteristic |
|---|---|
| 0.000 gm | None |
| 0.010 gm | Some fluorescence - gets better as drying takes place |
| 0.020 gm | Better than above - exhibited a yellow-green color |
| 0.030 gm | Excellent - clearly fluoresced to a yellow - green color |

This example shows that the inclusion of the stilbene derivative sold under the trademark EASTOBRITE® OB-1 in a chrome-free pretreatment fluorescences under an ultraviolet light, thereby indicating the presence of the pretreatment on the metal. According to this example, the stilbene derivative should be present in an amount of at least 0.010 grams/liter of working bath.

Although illustrated and described herein with reference to certain specific embodiments and examples, the present invention is nevertheless not intended to be limited to the details shown. Rather, the claims should be read to include various modifications within the scope and range of equivalents of the claims, without departing from the spirit of the invention.

What is claimed is:

1. A method for indicating the presence of a chrome-free pretreatment on a metal Surface comprising:

forming a mixture of a chrome-free pretreatment and an ultraviolet tracer, which are at least dispersible and soluble in water, said pretreatment comprising a polymeric resin and a group IV-B compound; and said ultraviolet tracer comprising a fluorescent whitening agent selected from the group consisting of at least one of a stilbene derivative and at least one of a coumarin derivative;

applying said mixture to a metal surface to form a coated metal surface; and exposing said coated metal surface to ultraviolet light, wherein said tracer exhibits a color upon exposure to ultraviolet light.

2. A method in accordance with claim 1, wherein said fluorescent whitening agent is a stilbene derivative.

3. A method in accordance with claim 1, wherein said fluorescent whitening agent is a coumarin derivative.

4. A method in accordance with claim 1, wherein said stilbene derivative is added to said chrome-free composition to a concentration of at least 0.010 grams/liter.

* * * * *

UNITED STATES PATENT AND TRADE MARK OFFICE
CERTIFICATE OF CORRECTION

PATENT NO. : 5,516,696
DATED : May 14, 1996
INVENTOR(S) : José B. Rivera

It is certified that error appears in the above-identified patent and that said Letters Patent is hereby corrected as shown below:

Cover page, item [75] change "Jos'''" to --José--.

In cover sheet, [56] change reference Mickols "5,000,802" to --5,100,802--.

Column 3, line 10, delete "Oakire" and insert --Oakite--.

Column 5, line 5, change "9rams" to read --grams--.

Column 6, line 8, change "Surface" to read --surface--.

Signed and Sealed this

Third Day of December, 1996

*Attest:*

BRUCE LEHMAN

*Attesting Officer*     *Commissioner of Patents and Trademarks*